United States Patent [19]
Okubo et al.

[11] Patent Number: 5,889,216
[45] Date of Patent: Mar. 30, 1999

[54] LIQUID HOLDING DEVICE AND METHOD OF MANUFACTURING THE SAME

[75] Inventors: Akio Okubo; Takao Fukuoka, both of Kyoto, Japan

[73] Assignee: Kyoto Daiichi Kagaku Co., Ltd., Kyoto, Japan

[21] Appl. No.: 71,036

[22] Filed: May 4, 1998

Related U.S. Application Data

[62] Division of Ser. No. 693,965, Aug. 7, 1996, Pat. No. 5,780,752.

[30] Foreign Application Priority Data

Aug. 9, 1995 [JP] Japan ........................................ 225699
Jun. 14, 1996 [JP] Japan ........................................ 175657

[51] Int. Cl.⁶ .................................................. C12M 1/18
[52] U.S. Cl. ............................................................. 73/863
[58] Field of Search .................... 73/61.41, 61.59, 73/64.56, 863; 356/36, 39–42, 437, 440–442, 244; 422/82.09, 99, 102, 104; 522/1

[56] References Cited

U.S. PATENT DOCUMENTS

| | | | |
|---|---|---|---|
| 3,949,121 | 4/1976 | Kenny | 427/98 |
| 4,634,659 | 1/1987 | Esumi et al. | |
| 4,798,706 | 1/1989 | Brigati | 422/102 |
| 4,803,154 | 2/1989 | Uo et al. | 435/7 |
| 5,041,266 | 8/1991 | Fox | 422/102 |
| 5,202,227 | 4/1993 | Matsuda et al. | 430/320 |
| 5,349,436 | 9/1994 | Fisch | 356/246 |

FOREIGN PATENT DOCUMENTS

A 3107964  9/1982  Germany.

OTHER PUBLICATIONS

Fujiwara et al., Patent No. 5,238,810; cover page and cols. 1–8, 61–62, and Figs. 45(a), 45(b), 46 only; Aug. 1993.

*Primary Examiner*—Robert Raevis
*Attorney, Agent, or Firm*—Finnegan, Henderson, Farabow, Garrett & Dunner, L.L.P.

[57] ABSTRACT

A simple device for holding liquid for an analysis of a liquid sample, said device comprising a material composed of organic macromolecule, having a surface divided into a plurality of areas which posses contact angles with regard to liquid that are different from each other, one of which is surrounded with the other. With regard to the analysis of test liquids, the device enables the easy holding of even minute quantities of liquid and offers sufficient quantitative precision for analysis.

2 Claims, 1 Drawing Sheet

F I G. 1 (A)
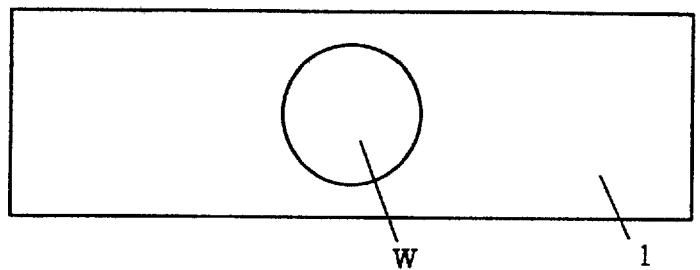
F I G. 1 (B)
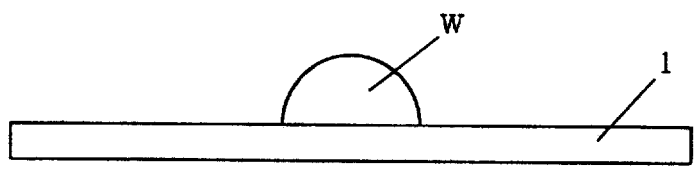
F I G. 2
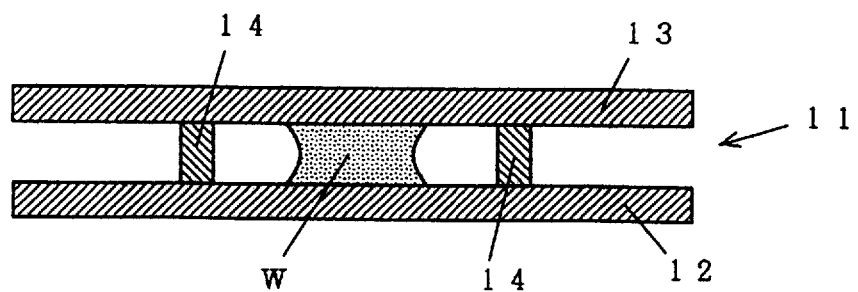

LIQUID HOLDING DEVICE AND METHOD OF MANUFACTURING THE SAME

This is a divisional of application Ser. No. 08/693.965, filed Aug. 7, 1996, now U.S. Pat. No. 5,780,752.

BACKGROUND OF THE INVENTION

1. Field of the Invention

This invention relates to a device for holding liquid (hereafter called a liquid holding device)for an analysis of a liquid sample and a method of manufacturing the said device. The liquid holding device of this invention is suitable for use as a clinical diagnostic tool in the measurement of the component of blood, urine, and other substances.

2. Description of the Related Art

The analysis of the component of a sample, when said sample is blood, urine, or another liquid, requires a vessel with which to contain the liquid or a holding device. Test tubes and other glass equipment are common containing vessels. A pipette is used to contain fixed quantities of the sample. As for holding devices, test pieces composed of liquid permeable paper, organic macromolecule film, and other substances are quite well known. In the case of such holding devices, a fixed amount of the test liquid is drawn up with a pipette and allowed to penetrate the test piece for holding.

Methods of using test tubes or other glass equipment to contain test liquids, however, create difficulty in gathering minute quantities of said liquid and hamper precision. Analyzing test liquid that has been allowed to penetrate the test piece requires the use of a pipette, which not only adds to the complexity of the operation, but does not allow miniaturization of machines that could be used in an attempt to automate the procedure.

SUMMARY OF THE INVENTION

The object of this invention, therefore, with regard to the analysis of test liquids, is to provide a simple liquid holding device that enables the easy holding of even minute quantities of liquid and offers sufficient quantitative precision for analysis.

To achieve the object described above, the liquid holding device concerned in this invention is equipped with material composed of organic macromolecule. The surface of the material is comprised of a multiplicity of areas which posses contact angles with regard to liquid that are different from each other. The first area forms a relatively small contact angle $\alpha$ against the surface of any liquid that has adhered to said area, (first area) to form a liquid sample and the second area, which is adjacent to the first area, forms a relatively large contact angle $\beta$ against the surface of the same liquid so that the liquid will not adhere to said area (second area).

An appropriate method for manufacturing the liquid holding device that enables liquid to be held for the analysis of liquid samples comprises the following main procedural features:

(a) A process by which organic macromolecule material is prepared.

(b) A process by which a mask with the given pattern is placed in a position that either forms close contact with the surface of the material or is separated from said surface.

(c) A process by which the surface of the material is irradiated with UV rays through the mask. The liquid held in the liquid holding device can include, in addition to the liquid sample that is to be analyzed, the liquid dissolving a reagent with which said liquid sample is to react.

BRIEF DESCRIPTION OF THE DRAWING

FIGS. 1(a) and 1(b) show the liquid holding device of actual embodiment 1 with water adhering to its surface. FIG.1 (a) is a top view and FIG. 1 (b) is a front view.

FIG. 2 shows a cross section of the liquid holding device of actual embodiment 2 with water adhering to its surface.

DETAILED DESCRIPTION OF THE INVENTION

The surface of the material or member of the liquid holding device of this invention comprised of a multiplicity of areas which possess contact angles, with regard to liquid, that are different from each other and existing adjacent to each other. Because of the difference of contact angles, if the quantity of liquid is minute, said liquid will adhere to the first area, which has a small contact angle (allowing liquid to readily wet it), and will not adhere to the second area, which has a large contact angle (making liquid more difficult to wet it).

If, for example, the area of the first area (with the small contact angle) is determined to a high level of precision and is surrounded by the second area (with a large contact angle), the quantity of liquid that adheres to the surface of the first area can be determined to a high degree of accuracy., in correlation to the area of the first area and the contact angle $\alpha$ formed by said liquid and the first area, regardless of the quantity of liquid that is supplied. This enables the said adhered liquid to be made a quantitative analysis by applying given quantity of reagent on it. Reagent can also be applied beforehand to the area with a small contact angle.

If the material used is two transparent sheets positioned facing each other and if the distance between said sheets is fixed by the spacers being intervened between said sheets, the first area is made the base and the liquid is held in the column form within the space sandwiched between the two pieces of material with placing the first area as a base. In such a case, a multiplicity of areas with different contact angles from each other are provided only on the surface of one of the said materials and the reagent can be applied to the surface of the other material. This enables the application of reagent before the adhesion of liquid, without altering the contact angle on the first area. Moreover, because the test liquid is held between two pieces of material, leakage of the test liquid is unlikely and workers are protected from any infection from the test liquid. This arrangement also prevents contamination of analysis equipment.

As explained above, the quantity of liquid that adheres to the surface of the material of the invention depends not only upon the surface area of the material but also on the contact angle. It is important to control the contact angle for each separate area of the material, during the production of the liquid holding device of this invention. If the liquid being held is water-based, for example, a good arrangement is that a large contact angle $\beta$ in the hydrophobic area would be of at least 60° and the difference between the contact angle in one area and the contact angle in an adjacent area ($\beta-\alpha$) would be of at least 30°. Within these parameters, the variance in the quantity of liquid that adheres over repeated trials is low. The contact angle can be controlled using UV irradiation conditions explained below, when the liquid holding device is produced using the irradiation.

To create multiple areas having different contact angles on the same surface of a single piece of material, a mask is made on the surface of hydrophobic (or hydrophilic), organic, macromolecule material, then a hydrophilic group (or hydrophobic group) and graft branches are chemically introduced to the part exposed by the mask. Plasma processing, corona discharge processing, and other methods can be employed instead of chemical processing to render only the exposed part of the surface hydrophilic (or hydrophobic), but the UV irradiation method described above is especially good as it does not require any special pre or post-treatment and the device used is simple.

One or more of the following can be used as the organic macromolecule for the material of the invention: polyethylene, polypropylene, polystyrene, ABS, poly(vinyl chloride), poly(vinylidene chloride), thermoplastic polyurethane, poly(methyl methacrylate), poly(ethylene oxide), fluororesin, polycarbonate, polyamide, acetal resin, poly(phenylene oxide), poly(butylene terephthalate), poly(ethylene terephthalate), poly(phenylene sulfide), or other thermoplastic resins; unsaturated polyester resin, epoxy resin, phenolic resin, urea resin, melamine resin, poly(diallyl phthalate), silicone resin, or other thermosetting resins; or silicone rubber or other rubbers.

The material can be shaped either in sheet, column, cylinder, gel, membrane, or fiber form. Basically, the material can be used if it is capable of securing an area having a small contact angle, in order to hold the test liquid. The shape of the area having a small contact angle is usually circular, with a diameter of between 1 and 7 mm; polygonal, with the length of one side being between 1 and 7 mm; or linear, with a width of between 1 and 5 mm. The optimal source of UV light for the producing method described above is a low-pressure mercury lamp. It is because the tube wall temperature should be low, approximately 100° C., and the tube will radiate high-energy, short-wavelength UV rays. Short-wavelength UV rays with wavelengths of 185 nm or 254 nm are good because they have high energy.

Radiation should usually be performed for a period of time between 1 and 120 minutes, at an irradiation distance of between 0.5 and 8.0 cm, and at an illumination intensity of between approximately 1 and 20 mW per cm$^2$.

DESCRIPTION OF THE PREFERRED EMBODIMENTS

EXAMPLE 1

Five sheets each of three kinds of material—poly(methyl methacrylate) (PMMA), poly(ethylene terphthalate) (PET), and polycarbonate (PC)—with a thickness of 0.5 mm each, two types of mask with a circular light-transmissive window having a diameter of 2 or 3 mm were prepared.

The materials were put through ultrasonic cleaning using a 50% aqueous ethanol solution, then dried. A mask was then placed on the surface of the material and a low-pressure mercury lamp was fixed at a height 2 cm perpendicularly above the material. The material was then irradiated with UV rays for 10 minutes, creating the first actual embodiment of the liquid holding device of this invention. Subsequent to the above process, the liquid holding device was immersed in water, then lifted gently, whereupon the water on the surface of the material was checked to verify that the water had adhered only in a circular shape corresponding to the light-transmissive window of the mask and thereby, that there were two adjacent areas on the surface of the material that had different contact angles with regard to said water and that were separated by a circular border. A top view and front view of said liquid holding device, while water is adhering to its surface, are shown in FIG. 1 (a) and FIG. 1 (b), respectively. The member of the device and water are shown as respectively symbol "1" and "W" in the drawings. The quantity of water adhering to the surface of this liquid holding device was measured using the Karl Fischer's Method. The results of the measurement are shown in Table 1.

Separately, to measure each of the contact angles for the two areas described above, 10 sheets of each of the three kinds of materials described above were prepared by washing them ultrasonically with a 50% aqueous ethanol solution. The materials were then dried. Next, 1.8 μl of water was dropped onto five sheets of each kind of material and the static contact angle was measured (prior to UV irradiation). The remaining five sheets of each material were exposed to UV irradiation under identical conditions as the actual embodiment of the liquid holding device described above, after which water was dropped on the irradiated parts in the same way as with the non-irradiated sheets. The static contact angle was then measured (posterior to UV irradiation). The results of these measurements are shown in Table 1.

TABLE 1

| Kind of material | | (n = 5) | |
| --- | --- | --- | --- |
| | FMMA | PET | PC |
| Diameter of mask window (mm) | 3 | 2 | 2 |
| Static contact angle (degree) | | | |
| Prior to UV irradiation | 79 | 77 | 94 |
| Posterior to UV irradiation | 31 | 42 | 23 |
| Quantity of water adhered (μg) | 1927.0 ±51.1 | 876.4 ±30.8 | 532.2 ±29.4 |

As can be seen in Table 1, the actual embodiment of the liquid holding device described above can hold minute fixed amount of water, even of the submicroliter order, with high accuracy. The holding capacity of the liquid holding device can be altered not only by changing the amount of surface area irradiated by UV rays but also by controlling the contact angle. Each of the materials of this actual embodiment was transparent, thus enabling absorptiometry to be performed by having the adhering water absorb light and measuring the amount of light that passes through the material. The existence of the two areas having different contact angles cannot be verified macroscopically prior to the immersion of the material in water. The border between the two areas can be recognized, however, if a line is drawn along the inner circumference of the light-transmissive window on the mask, prior to subjecting the material to UV irradiation.

EXAMPLE 2

The second actual embodiment of the liquid holding device of this invention will be explained along with a drawing. FIG. 2 is a cross section of the second embodiment of the liquid holding device of this invention. In this example, the liquid holding device 11 is composed of two sheets of material 12 and 13 situated facing each other and spacers 14 that fix the distance separating material 12 from material 13.

Materials 12 and 13 are both transparent polystyrene (PS) sheets having a thickness of 1 mm and a contact angle of 90° with water adhered to their surfaces. Only a circular area (not shown in the drawing), having a diameter of 3 mm and located in the center of the surface of each of the sheets 12 and 13, has had its hydrophilic properties enhanced to create an 15° contact angle with water. Material 13 has had reagent applied within the circular area. Liquid holding device 11 was produced according to the following procedures. First, the relationship between the UV irradiation conditions (e.g., irradiation time) for PS and contact angle were found by experimentation. A polystyrene sheet was washed ultrasonically with a 50% aqueous ethanol solution and dried, then set in a UV irradiation device. A mask having a circular light-transmissive window of 3 mm in diameter was positioned on top of the sheet, above which a low-pressure mercury lamp was fixed. The material was then irradiated with UV rays through the mask until a 15° contact angle for water on the circular area was obtained. Separately, a reagent solution was prepared having the following composition.

Peroxidase: 4,000 units

Glucose oxidase: 4,000 units

4-Aminoantipyrine: 10 mg

1-Naphthol 3, 6-sodium disulfonate: 12 mg 0.1M phosphate buffer solution (pH: 6): 3 ml Polyvinyl pyrrolidone: 50 mg After UV irradiation, a single 1 μl drop of reagent solution was dropped inside the circular area on the sheet, then the sheet was dried, creating material 13. Material 12 was created in the same way, except that no reagent was dropped. The areas on material 12 and material 13 that were exposed to UV rays were positioned facing each other and spacers 14 were intervened and fixed in place such that the clearance between the two sheets of material 12 and 13 was 0.3 mm. This completed the production of the second embodiment of the liquid holding device 11 of this invention.

An aqueous glucose solution was poured through the space between materials 12 and 13. The result was that the glucose aqueous solution(shown as symbol "W" in the drawing) adhered only to the above-described circular areas on each of the materials, as shown in FIG. 2, and was held in cylindrical form. After allowing the liquid holding device to remain as is for one minute, light with a wavelength of 550 nm was beamed perpendicularly through the circular areas on materials 12 and 13 and the absorbency was measured. The results of measuring absorbency using three different concentrations of aqueous glucose solution are shown in Table 2.

TABLE 2

| Glucose concentration (mg/dl) | Absorbency Average value ± S.D. |
|---|---|
| 100 | 0.102 ± 0.006 |
| 200 | 0.187 ± 0.009 |
| 400 | 0.390 ± 0.017 |

As can be seen in Table 2, absorbency has a nearly proportional correlation with the concentration of the aqueous glucose solution. These results confirm that the quantity of aqueous glucose solution held between materials 12 and 13 is constant.

What is claimed is:

1. A method of manufacturing a device for holding liquid for an analysis of a liquid sample, comprising the steps of:
   (a) preparing a organic macromolecule material,
   (b) placing a mask with a given pattern in a position that either forms close contact with the surface of the material or is separated from said surface,
   (c) irradiating the surface of the material with ultraviolet (UV) rays through the mask.

2. The method according to claim 1, wherein the mask is patterned such that the part that allows UV rays to penetrate is surrounded by a part that blocks UV rays.

* * * * *